United States Patent
Georges et al.

(10) Patent No.: US 7,615,681 B2
(45) Date of Patent: Nov. 10, 2009

(54) METHODS FOR MODIFYING PLANT RESPONSES TO STRESS AND CORRESPONDINGLY DERIVED PLANTS

(75) Inventors: Fawzy Georges, Saskatoon (CA); Shankar Das, Sakatoon (CA); Atta Hussain, Saskatoon (CA)

(73) Assignee: National Research Council of Canada, Ottawa, Ontario (CA)

( * ) Notice: Subject to any disclaimer, the term of this patent is extended or adjusted under 35 U.S.C. 154(b) by 666 days.

(21) Appl. No.: 10/503,223

(22) PCT Filed: Feb. 5, 2003

(86) PCT No.: PCT/CA03/00157

§ 371 (c)(1),
(2), (4) Date: Aug. 2, 2004

(87) PCT Pub. No.: WO03/066846

PCT Pub. Date: Aug. 14, 2003

(65) Prior Publication Data

US 2007/0011782 A1    Jan. 11, 2007

Related U.S. Application Data

(60) Provisional application No. 60/353,966, filed on Feb. 5, 2002.

(51) Int. Cl.
*A01H 1/00*    (2006.01)
*C07H 21/04*    (2006.01)
*C07K 14/415*    (2006.01)
*C12N 15/00*    (2006.01)

(52) U.S. Cl. ............... 800/289; 435/6; 435/468; 435/419; 435/320.1; 435/183; 530/370; 536/23.1; 536/23.6; 800/278; 800/290; 800/295

(58) Field of Classification Search .......... 435/6, 435/69.1, 468, 419, 252.3, 320.1, 183; 530/370; 536/23.6, 24.1; 800/278, 295, 289, 281
See application file for complete search history.

(56) References Cited

U.S. PATENT DOCUMENTS 5,474,921 A * 12/1995 Koblan et al. ............... 435/196
6,720,477 B2 * 4/2004 da Costa e Silva et al. .. 800/289

OTHER PUBLICATIONS

Shi et al. The Plant Journal, 1995, vol. 8, No. 3, pp. 381-390.*
Das et al., GeneEmbl, Accession No. AF108123, Direct submission, Apr. 20, 1999, see Result 2.*

* cited by examiner

*Primary Examiner*—Phuong T Bui
(74) *Attorney, Agent, or Firm*—Hans Koenig

(57) ABSTRACT

Plant stresses such as pest drought, and excessive temperatures can lead to significant losses of crops each year. There is a continuing need to develop novel plant varieties that are less susceptible to damage or loss by such stresses. The present invention provides a system and method for generating plants having an increased resistance to plant stresses such as drought or adverse temperatures. Transgenic plants expressing a phosphoinositide-specific phospholipase C (PI-PLC) gene can show an unexpected and dramatic improvement in their capacity to tolerate a variety of stress conditions. Moreover, increased PI-PLC expression can further lead to marked increase in plant growth rates, maturation, and lipid content. The present invention encompasses transgenic plants having modifications with regard to PI-PLC pathways, such as altered PI-PLC levels, and plant products thereof.

14 Claims, 9 Drawing Sheets

SEQUENCE LISTING

<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: Primer 1

<400> SEQUENCE: 1
catgtcgaag caaacgtaca aagt                                              24

<210> SEQ ID NO 2
<211> LENGTH: 24
<212> TYPE: DNA
<213> ORGANISM: Artificial
<220> FEATURE:
<223> OTHER INFORMATION: Primer 2

<400> SEQUENCE: 2
acacaaactc caccttcacg agaa                                              24

<210> SEQ ID NO 3
<211> LENGTH: 1746
<212> TYPE: DNA
<213> ORGANISM: Brassica napus

<400> SEQUENCE: 3
atgtcgaagc aaacgtacaa agtgtgtttc tgctttaacc ggaggttccg gtacaccgca        60
tcggaggcgc cgcgtgatgt caagacccct ttcgacaagt actcggagaa tggcgtcatg       120
accgtggatc atctccagag gtttctgatc gatgttcaga agcaagataa agccactaaa       180
gaggatgcgc agtcaatcat caacgccgcg tcttcgcttc ttcatagtaa cggtctccac       240
ctcgatgctt tcttcaagta tcttttggt gacagtaacc ctccgcttgc tcttcatgag        300
gtgcatcaag acatggatgc tcctatatca cattatttca tattcaccgg tcacaattca       360
tatttaaccg gcaaccagct gagcagtgac tgcagtgagg tgcctattat agatgcattg       420
aagaaaggtg tcagggtgat tgagttggat atatggccta actcaaacaa aaacgatatt       480
gatgttcttc acggaaggac tctcacttca cctgtggagt taatcaagtg tctaagagct       540
atcaaaacac atgcattcga agtatctgac taccctgttg ttgtcactct tgaggatcat       600
ctcactccag aacttcagtc caaagttgct gagatggtta ccgagatatt tggagagatc       660
ttgtttactc ctcctgtggg agaatctttg aaggagttcc catcaccaaa ctcattaaaa       720
agacggatca tcatctcaac aaagccacca aagaatataca aggaaggaaa ggatgaggat       780
gtggtgcaga aaggtaaagc cttgggtgat gaagaagttt ggggagaga agttccaagt        840 tttattgaga ggaacaaaag tggtgacaag atgacttag atgatgagga ggataatgat       900
gaagatgatg atgtagagaa gttcaagaag aatgcaccac cgcaatataa acatttgatt       960
gcaatccatg ctgggaaacc aaaaggtagt attactgcgt gcttgaaggt agatcctgat      1020
aaggtaagac gccttagctt gagcgaggaa caactagaaa aggcagcaga aaaatatgct      1080
aaacagattg tgaggtttac gcagcagaat ctgctgagga tttacccaaa ggaactaga       1140 gtgacttcat caaactacaa cccattggtt gggtggagcc acggtgctca aatggtggct      1200
ttcaacatgc agggatatgg aagatcatta tggctaatgc aaggaatgtt tagagccaat      1260
ggcggatgtg gatacatcaa gaaaccagat attctcttaa aaggtggctc agatagtgac      1320

-continued

```
atctttgacc caaaaactac tctacctgta aaacaacac taagggtaac catatacatg    1380
ggagaaggct ggtactttga cttccgccac acacacttcg atcaatactc acctcctgac    1440
ttctacacga gggtggggat agctggagtt ccagcggata cggttatgaa gaagacaaag    1500
acgctagagg ataactgggt gccatcttgg gatgaggtgt ttgagttccc actaacggtc    1560
ccagagctgg ctctactgcg gttagaagtg catgagtatg acatgtcgga aaggatgat     1620 tttggaggtc agacatgttt gcctgtttgg gagctgcagg aaggaataag atcgtttcct    1680
ttacataacc gcaaagagga gaagtacaaa tctgttaagc ttctcgtgaa ggtggagttt    1740
gtgtga                                                              1746
```

<210> SEQ ID NO 4
<211> LENGTH: 276
<212> TYPE: PRT
<213> ORGANISM: Brassica napus

<400> SEQUENCE: 4

```
Met Ser Lys Gln Thr Tyr Lys Val Cys Phe Cys Phe Asn Arg Arg Phe
1               5                   10                  15

Arg Tyr Thr Ala Ser Glu Ala Pro Arg Asp Val Lys Thr Leu Phe Asp
            20                  25                  30

Lys Tyr Ser Glu Asn Gly Val Met Thr Val Asp His Leu Gln Arg Phe
        35                  40                  45

Leu Ile Asp Val Gln Lys Gln Asp Lys Ala Thr Lys Glu Asp Ala Gln
    50                  55                  60

Ser Ile Ile Asn Ala Ala Ser Ser Leu Leu His Ser Asn Gly Leu His
65                  70                  75                  80

Leu Asp Ala Phe Phe Lys Tyr Leu Phe Gly Asp Ser Asn Pro Pro Leu
                85                  90                  95

Ala Leu His Glu Val His Gln Asp Met Asp Ala Pro Ile Ser His Tyr
            100                 105                 110

Phe Ile Phe Thr Gly His Asn Ser Tyr Leu Thr Gly Asn Gln Leu Ser
        115                 120                 125

Ser Asp Cys Ser Glu Val Pro Ile Ile Asp Ala Leu Lys Lys Gly Val
    130                 135                 140

Arg Val Ile Glu Leu Asp Ile Trp Pro Asn Ser Asn Lys Asn Asp Ile
145                 150                 155                 160

Asp Val Leu His Gly Arg Thr Leu Thr Ser Pro Val Glu Leu Ile Lys
                165                 170                 175

Cys Leu Arg Ala Ile Lys Thr His Ala Phe Glu Val Ser Asp Tyr Pro
            180                 185                 190

Val Val Val Thr Leu Glu Asp His Leu Thr Pro Glu Leu Gln Ser Lys
        195                 200                 205

Val Ala Glu Met Val Thr Glu Ile Phe Gly Glu Ile Leu Phe Thr Pro
    210                 215                 220

Pro Val Gly Glu Ser Leu Lys Glu Phe Pro Ser Pro Asn Ser Leu Lys
225                 230                 235                 240

Arg Arg Ile Ile Ile Ser Thr Lys Pro Pro Lys Glu Tyr Lys Glu Gly
                245                 250                 255

Lys Asp Glu Asp Val Val Gln Lys Gly Lys Ala Leu Gly Asp Glu Glu
            260                 265                 270

Val Trp Gly Arg
        275
```

US 7,615,681 B2

METHODS FOR MODIFYING PLANT RESPONSES TO STRESS AND CORRESPONDINGLY DERIVED PLANTS

This application is a National Stage application of PCT Application PCT/CA03/00157 filed Feb. 5, 2003 which claims benefit of U.S. Provisional Application 60/353,966 filed Feb. 5, 2002.

FIELD OF THE INVENTION

The present invention relates to the field of plant stress tolerance, and means to alter plant metabolism to improve plant resistance to adverse environmental conditions, including drought and extreme temperatures. The invention further relates to processes for generating modified plants that exhibit increased stress tolerance, to the plants generated by such processes, and their products.

BACKGROUND TO THE INVENTION

Abiotic stresses such as salt, drought and low temperature are the most limiting and least controllable factors in crop production. From a world perspective these stresses have the most significant impact on yield. As more land becomes salinized through poor water quality, salinity impacts on crop production is becoming increasingly important worldwide (Winicov, 1998). Continued use of fresh water has significantly and, in some cases, alarmingly lowered the water table in many cropland areas, forcing low-water regimes on growing plants and leading to poor performance. Among many affected areas around the world, prairie lands by nature, appear to be very prone to such phenomenon. Recent drought in Saskatchewan, a land that produces the best quality wheat and canola, has severely affected the crop yield. Finally, low temperature impact on plant performance and low yield world wide and, in particular, in the prairie provinces is a persistent problem.

There exists a continuing need to develop plants and crops that exhibit improved resistance to plant stresses, thereby increasing crop yields in adverse conditions and reducing the risk of crop failure. For example, plants with increased tolerance to drought, extreme temperatures and higher salt conditions may open the possibility of farming in semi-desert climates, where agriculture was previously non-viable. In addition, the development of novel crops with improved tolerance to cold or freezing temperatures may significantly prolong the growing season in regions with colder climates.

A number of plant genes are known to show increased levels of expression when plants are exposed to stress. However, despite considerable efforts to engineer genetically modified crops with increased stress tolerance, to date there are little or no such crops on the commercial market.

The future prospects of engineering novel plants with an increased capacity to tolerate environmental insults will depend on the modulation of critical stress tolerance controlling genes, and knowledge of their functional regulatory properties. The inventors for the present application, and others, have endeavored to decipher the mechanisms of plant stress tolerance in the hope of developing an understanding of the biochemical pathways involved. Nonetheless, the characterization of the genes and proteins involved in plant stress responses presents a number of significant challenges.

There remains a continuing need to develop a better understanding of plant stress responses, so that corresponding methods can be developed to confer advantageous properties to plants. This need extends to the production of crops that exhibit resistance to damage by adverse climatic conditions such as excessive temperatures, drought, and conditions of high salinity. Even incremental gains in plant stress tolerance may have a significant economic impact in stabilizing the quality and supply of grain, oilseed and horticulture. Enhancement of germination, growth and flowering are extremely important in regions that have a short or otherwise difficult growing season.

SUMMARY OF THE INVENTION

It is an object of the present invention, at least in preferred forms, to provide a system and a method for the genetic modification of a plant, to increase the resistance of the plant to adverse conditions such as drought and/or excessive temperatures, compared to an unmodified plant.

It is another object of the present invention, at least in preferred forms, to provide a transgenic plant that exhibits increased resistance to adverse conditions such as drought and/or excessive temperatures compared to an unmodified plant.

It is another object of the present invention, at least in preferred forms, to provide a system and method of modifying a plant, to alter the growth potential or development of the plant.

It is another object of the present invention, at least in preferred forms, to provide a system and method for enhancing the capacity of a plant to modulate guard cell activity in response to water stress.

It is an object of the invention to enhance the ability of non-tolerant plants to modulate their guard cell activity in response to water stress by over-expressing the gene for PI-PLC in *B. napus* under the influence of an inducible promoter (e.g. Dc3, or using a guard cell-specific regulatory sequence, etc.). The enhanced PLC activity would in turn be expected to lead to elevated amounts of $IP_3$, thereby increasing cytosolic $Ca^{2+}$, in a manner that is analogous to the natural mechanism of protection exerted by tolerant plants.

The inventors have succeeded in the development of a system and a method for plant modification to enhance the capacity of a plant to respond to water stress brought about, for example, by conditions of drought or excessive temperatures.

Specifically, the systems and methods of the present invention pertain to the manipulation of a gene encoding for Phosphoinositide-Specific Phospholipase C (PI-PLC).

The inventors have now successfully accomplished constitutive over-expression of PI-PLC in all tissues of *Brassica napus*, which also includes targeting the gene into guard cells.

The approach includes, at least in preferred embodiments, the targeting of an enzyme involved in signal perception, spatially to a site (guard cells) where an artificially produced signal will trigger a rise in $IP_3$, which, through a series of steps performed by the cell as a result, will lead to a reduction in stomatal water loss. In addition, the inventors have observed additional favourable characteristics including early maturation of plants that may contribute to a shortened growing season without yield penalties.

In a first aspect, the present invention provides a method of generating a transgenic plant having an altered stress response or an altered phenotype compared to an unmodified plant, characterized in that the method comprises the steps of:
(a) introducing into a plant cell capable of being transformed and regenerated into a whole plant a construct comprising, in addition to the DNA sequences required for transformation and selection in plants, an expression construct including a DNA sequence encoding a Phosphoinositide-Specific Phospholipase C (PI-PLC) operatively linked to a promoter for expressing said DNA sequence; and (b) recovery of a plant which contains the expression construct.

Preferably, the expression construct further includes targeting means for targeting the activity of the PI-PLC expressed from the construct to guard cells of the plant.

Preferably, the targeting means comprises an inducible, guard cell-specific promoter for specific expression of the DNA sequence within guard cells of the plant. Preferably, the targeting means comprises a signal sequence encoded by said expression construct comprising a series of amino acids covalently linked to said PI-PLC upon expression of said DNA sequence.

Preferably, the transgenic plant generated by the methods exhibits an altered stress response selected from the group consisting of: increased tolerance to heat, increased tolerance to cold; increased tolerance to drought. Preferably, the transgenic plant exhibits an altered phenotype selected from the group consisting of: early maturation, increased growth rate, increased biomass, and increased lipid content.

In accordance with the methods of the present invention, the DNA sequence preferably encodes a Phosphoinositide-Specific Phospholipase C (PI-PLC) is derived from a plant of the genus *Brassica*. More preferably the DNA sequence encoding a Phosphoinositide-Specific Phospholipase C (PI-PLC) is derived from a plant of the species *Brassica napus*. Preferably the DNA sequence encoding a Phosphoinositide-Specific Phospholipase C (PI-PLC) encodes a peptide having at least 70%, more preferably at least 90%, more preferably at least 95% identity to the peptide of SEQ ID NO: 4. In an alternative aspect, DNA sequence encoding a Phosphoinositide-Specific Phospholipase C (PI-PLC) is oriented in an antisense direction relative to said promoter within said construct.

In accordance with the methods of the present invention, the promoter is preferably selected from the group consisting of an constitutive promoter, an inducible promoter, a strong promoter, a weak promoter, a tissue specific promoter, a tissue-inspecific promoter, and organ specific promoter, a cell-specific promoter. More preferably the promoter is a constitutive promoter for overexpressing said DNA sequence encoding a Phosphoinositide-Specific Phospholipase C (PI-PLC). Preferably the promoter is suitable for overexpressing said DNA sequence encoding a Phosphoinositide-Specific Phospholipase C (PI-PLC) within guard cells of said transgenic plant. More preferably the promoter is a guard-cell specific promoter derived from a plant of the genus *Brassica*.

In another aspect, the present invention provides a method of generating a transgenic plant having an altered stress response or an altered phenotype compared to an unmodified plant, characterized in that the method comprises the steps of:

(a) introducing into a plant cell capable of being transformed and regenerated into a whole plant a construct comprising, in addition to the DNA sequences required for transformation and selection in plants, an expression construct including a DNA sequence encoding a factor from the Phosphoinositide-Specific Phospholipase C (PI-PLC) pathway operatively linked to a promoter for expressing said DNA sequence; and (b) recovery of a plant which contains the expression construct.

In another aspect, the present invention provides a transgenic plant that exhibits an altered stress response or an altered phenotype relative to an unmodified plant, characterized in that the transgenic plant includes an expression cassette comprising a DNA sequence encoding a Phosphoinositide-Specific Phospholipase C (PI-PLC) operatively linked to a promoter for expressing said DNA sequence in said transgenic plant. Preferably the transgenic plant exhibits an altered stress response compared to an unmodified plant selected from the group consisting of increased tolerance to heat, increased tolerance to cold; increased tolerance to salt and high salinity, increased tolerance to drought. Preferably the plant exhibits an altered phenotype compared to an unmodified plant, said altered phenotype selected from the group consisting of early maturation, increased growth rate, increased biomass, and increased lipid content.

Preferably the plant exhibits an altered stress response selected from the group consisting of: decreased tolerance to heat, decreased tolerance to cold; decreased tolerance to salt and high salinity, decreased tolerance to drought. Alternatively, the plant preferably exhibits an altered phenotype compared to an unmodified plant, said altered phenotype selected from the group consisting of decreased growth rate, decreased biomass, and decreased lipid content. Preferably, the plant is a grass.

In another aspect, the present invention provides a transgenic plant that exhibits an altered stress response or an altered phenotype relative to an unmodified plant, characterized in that the transgenic plant includes an expression cassette comprising a DNA sequence encoding a factor from the Phosphoinositide-Specific Phospholipase C (PI-PLC) pathway operatively linked to a promoter for expressing said DNA sequence in said transgenic plant.

In another aspect, the present invention provides a method of identifying whether a plant that has been successfully transformed with a construct, characterized in that the method comprises the steps of:

(a) introducing into plant cells capable of being transformed and regenerated into whole plants a construct comprising, in addition to the DNA sequences required for transformation and selection in plants, an expression construct that includes a DNA sequence encoding a Phosphoinositide-Specific Phospholipase C (PI-PLC) operatively linked to a promoter for expressing said DNA sequence;

(b) regenerating the plant cells into whole plants; and (c) subjecting the plants to a screening process to differentiate between transformed plants and non-transformed plants.

Preferably the screening process involves subjecting the plants to environmental conditions suitable to kill non-transformed plants, retain viability in transformed plants.

In another aspect, the present invention provides a kit for generating a transgenic plant having an altered stress response or an altered phenotype compared to an unmodified plant, characterized in that the kit comprises:

an expression construct including a DNA sequence encoding a Phosphoinositide-Specific Phospholipase C (PI-PLC) operatively linked to an promoter suitable for expressing said DNA sequence in a plant cell;

whereby said transgenic plant is recovered from a plant cell transformed with said expression construct.

Preferably the kit further includes targeting means for targeting the activity of the PI-PLC expressed from the construct to guard cells of the plant. Preferably the targeting means comprises an inducible, guard cell-specific promoter for specific expression of the DNA sequence within guard cells of the plant. Alternatively the targeting means preferably comprises a signal sequence encoded by said expression construct and comprising a series of amino acids covalently linked to said PI-PLC upon expression of said DNA sequence.

In accordance with the kit of the present invention, the transgenic plant preferably exhibits an altered stress response selected from the group consisting of: increased tolerance to heat, increased tolerance to cold; increased tolerance to salt and high salinity, increased tolerance to drought. Alternatively the transgenic plant preferably exhibits an altered phenotype selected from the group consisting of early maturation, increased growth rate, increased biomass; and increased lipid content. Preferably the DNA sequence encodes a Phosphoinositide-Specific Phospholipase C (PI-PLC) is derived from a plant from the genus *Brassica*. Preferably the DNA sequence encodes a Phosphoinositide-Specific Phospholipase C (PI-PLC) is derived from a plant from the species *Brassica napus*. More preferably the DNA sequence encoding a Phosphoinositide-Specific Phospholipase C (PI-PLC) encodes a peptide having at least 70%, more preferably at least 90%, more preferably at least 95% identity to the peptide of SEQ ID NO: 4. Preferably said DNA sequence encoding a Phosphoinositide-Specific Phospholipase C (PI-PLC) is oriented in an antisense direction relative to said promoter within said construct.

In accordance with the kit of the present invention, the promoter is preferably selected from the group consisting of an constitutive promoter, an inducible promoter, a strong promoter, a weak promoter, a tissue specific promoter, a tissue-inspecific promoter, and organ specific promoter, a cell-specific promoter. Preferably the promoter is a constitutive promoter for overexpressing said DNA sequence encoding a Phosphoinositide-Specific Phospholipase C (PI-PLC). Preferably the promoter is suitable for over expressing said DNA sequence encoding a Phosphoinositide-Specific Phospholipase C (PI-PLC) within guard cells of said transgenic plant. Preferably the promoter is a guard-cell specific promoter derived from a plant of the genus *Brassica*.

In another aspect, the present invention provides a nucleotide sequence encoding a Phosphoinositide-Specific Phospholipase C (PI-PLC), characterized in that the nucleotide sequence encodes a peptide having at least 70%, more preferably 90%, more preferably 95%, most preferably 99% identity to the peptide sequence of SEQ ID NO: 4.

The present invention encompasses method and kits that utilize factors involved in Phosphoinositide-Specific Phospholipase C (PI-PLC) pathways. The invention is in no way intended to be limited with regard to the source of the PI-PLC, nor the plant species that is modified using the methods and kits of the invention. Moreover, the invention encompasses the use of other factors involved in the PI-PLC-specific pathways, in addition to PI-PLC itself.

DEFINITIONS

Figure 1:
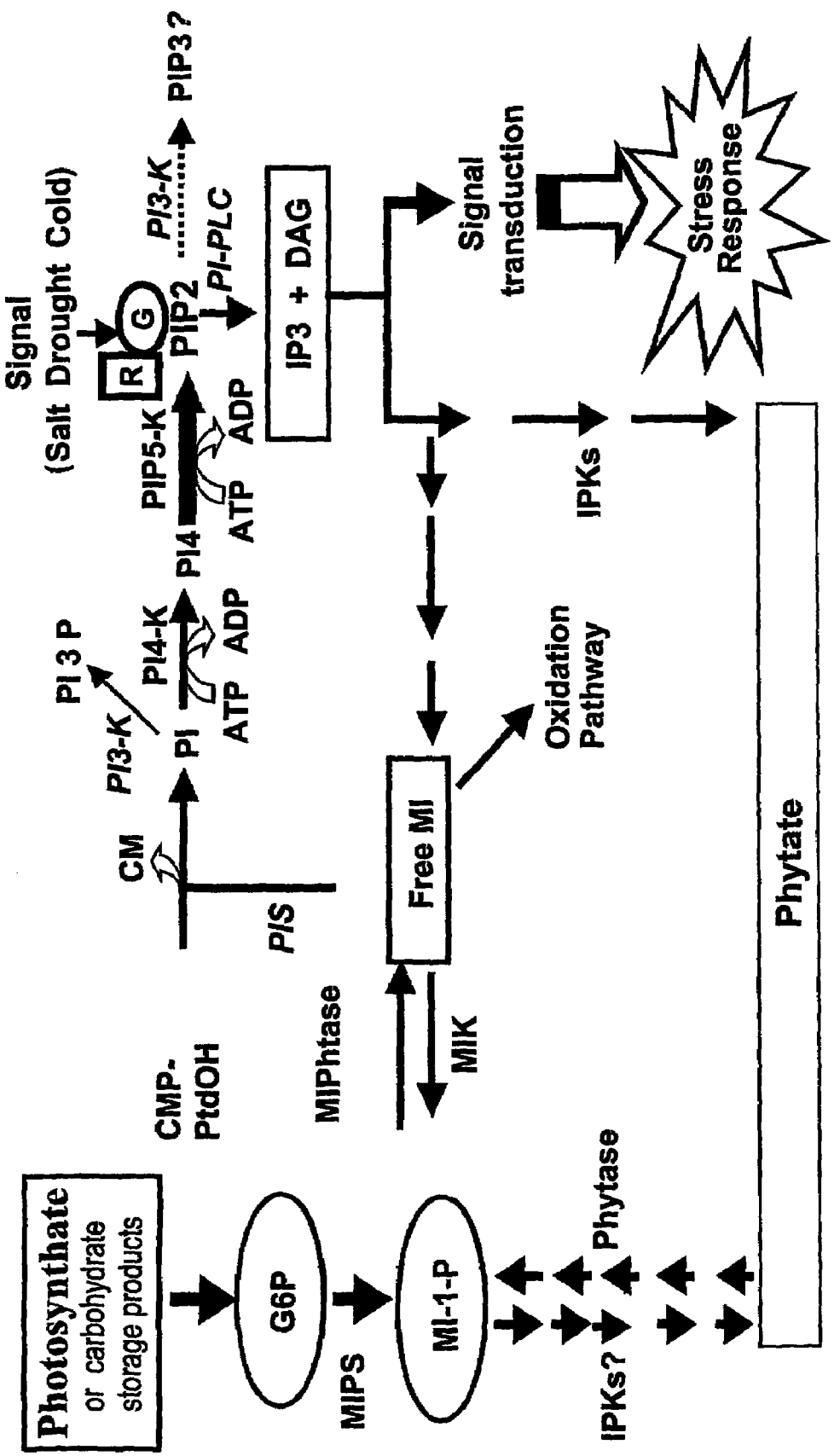
FIG. 1 schematically illustrates various metabolic pathways involved in stress responses in plants, including the phosphoinositol bisphosphate pathway, and phytate metabolism.
Figure 2:
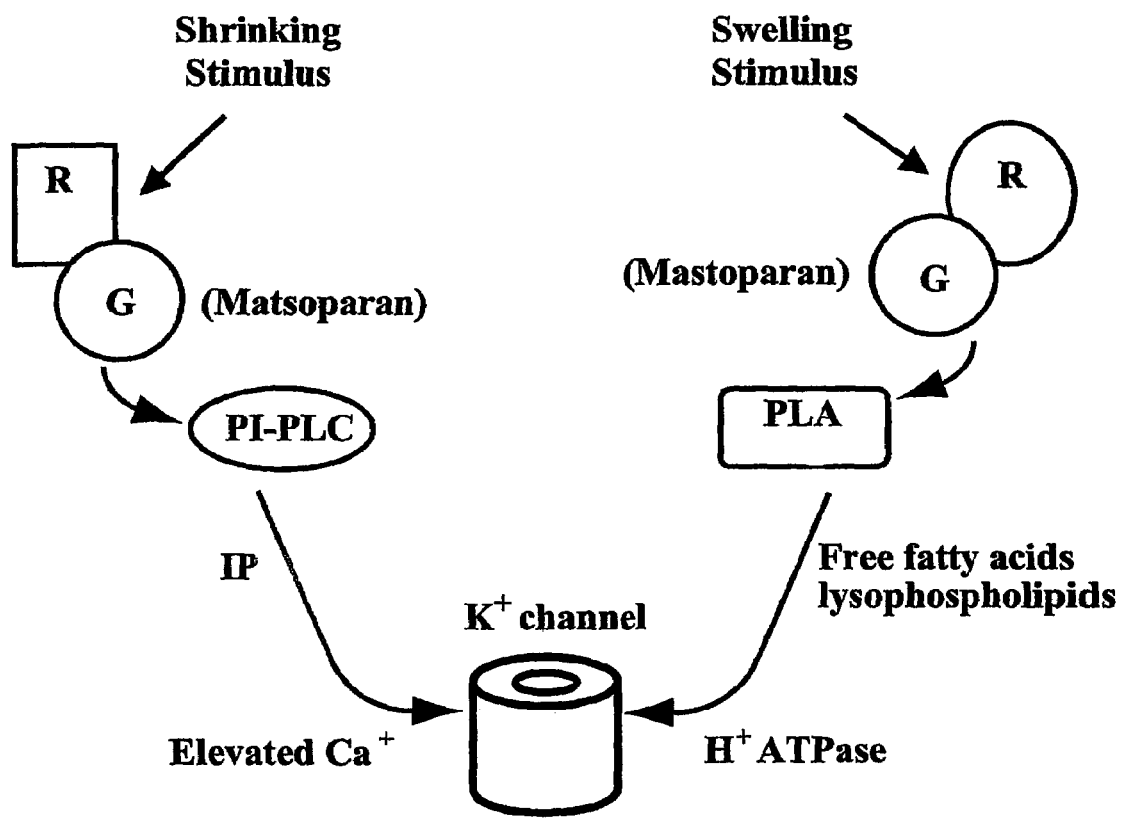
FIG. 2 schematically illustrates phospholipase-mediated cell volume changes in guard cells.

The singular forms "a," "an," and "the" include plural reference unless the context clearly dictates otherwise.

A "coding sequence" or "coding region" is the part of a gene that codes for the amino acid sequence of a protein, or for a functional RNA such as a tRNA or rRNA. A coding sequence typically represents the final amino acid sequence of a protein or the final sequence of a structural nucleic acid. Coding sequences may be interrupted in the gene by intervening sequences, typically intervening sequences are not found in the mature coding sequence.

"Exogenous" gene expression pertains to the expression of a gene sequence within a cell, or within the cells of an organism, wherein the gene sequence has been introduced artificially into the cell or organism (e.g. by transformation/transfection). Exogenous gene expression contrasts to "endogenous" gene expression, which occurs from within the wild-type genome of the cell. The presence of the exogenous gene sequence may confer properties to the modified cell or organism that are not present in a corresponding unmodified cell or organism. A gene may be exogenously expressed from a gene cassette that forms part of an expression construct. Moreover, the expression construct may remain independent from the endogenous DNA of the cell(s), or may become more stably integrated into the genome of the cell(s).

A "bicistronic" vector or a "bicistronic" construct encompasses an transformable DNA sequence having at least two promoter sequences. In the case of the bicistronic construct, each promoter sequence is operatively linked to a coding sequence to form a gene cassette, such that expression of each gene cassette results in the production of a corresponding ribonucleic acid. The term "bicistronic" is intended to encompass "multicistronic", such that multicistronic constructs may include multiple gene cassettes.

A "polynucleotide encoding an amino acid sequence" refers to a nucleic acid sequence that encodes the genetic code of at least a portion of a mature protein sequence, typically a contiguous string of amino acids typically linked through a peptide bond. An "amino acid sequence" is typically two or more amino acid residues, more typically 10 or more amino acids in a specific defined order.

A "complement" or "complementary sequence" is a sequence of nucleotides which forms a hydrogen-bonded duplex with another sequence of nucleotides according to Watson-Crick base-pairing rules. For example, the complementary base sequence for 5'-AGCT-3' is 3'-TCGA-5'.

"Expression" refers to the transcription of a gene into structural RNA (rRNA, tRNA) or messenger RNA (mRNA) with subsequent translation into a protein in the case of the mRNA.

Polynucleotides are "functionally equivalent" if they perform substantially the same biological function. By substantially the same biological function it is meant that similar protein activities or protein function are encoded by a mRNA polynucleotide, or a structural polynucleotide has a similar structure and biological activity.

Polynucleotides are "heterologous" to one another if they do not naturally occur together in the same arrangement in the same organism. A polynucleotide is heterologous to an organism if it does not naturally occur in its particular form and arrangement in that organism.

Polynucleotides or polypeptides have "homologous" or "identical" sequences if the sequence of nucleotides or amino acid residues, respectively, in the two sequences is the same when aligned for maximum correspondence as described herein. Sequence comparisons between two or more polynucleotides or polypeptides are generally performed by comparing portions of the two sequences over a portion of the sequence to identify and compare local regions. The comparison portion is generally from about 20 to about 200 contiguous nucleotides or contiguous amino acid residues or more. The "percentage of sequence identity" or "percentage of sequence homology" for polynucleotides and polypeptides, such as 50, 60, 70, 80, 90, 95, 98, 99 or 100 percent sequence identity may be determined by comparing two optimally aligned sequences which may or may not include gaps for optimal alignment over a comparison region, wherein the portion of the polynucleotide or polypeptide sequence in the comparison may include additions or deletions (i.e., gaps) as compared to the reference sequence (which does not comprise additions or deletions) for optimal alignment of the two sequences.

The percentage of homology or similarity is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F. et al 1990. J. Mol. Biol. 215:403; Altschul, S. F. et al 1997. Nucleic Acids Res. 25: 3389-3402) and ClustalW programs. BLAST is available on the Internet at www.ncbi.nlm.nih.gov and a version of ClustalW is available at www2.ebi.ac.uk. Other suitable programs include GAP, BESTFIT, FASTA, and TFASTA in the Wisconsin Genetics Software Package (Genetics Computer Group (GCG), 575 Science Dr., Madison, Wis.). For greater certainty, as used herein and in the claims, "percentage of sequence identity" or "percentage of sequence homology" of amino acid sequences is determined based on optimal sequence alignments determined in accordance with the default values of the BLASTX program, available as described above.

Sequence identity typically refers to sequences that have identical residues in order, whereas sequence similarity refers to sequences that have similar or functionally related residues in order. For example an identical polynucleotide sequence would have the same nucleotide bases in a specific nucleotide sequence as found in a different polynucleotide sequence. Sequence similarity would include sequences that are similar in character for example purines and pyrimidines arranged in a specific fashion. In the case of amino acid sequences, sequence identity means the same amino acid residues in a specific order, where as sequence similarity would allow for amino acids with similar chemical characteristics (for instance basic amino acids, or hydrophobic amino acids) to reside within a specific order.

The terms "stringent conditions" or "stringent hybridization conditions" includes reference to conditions under which a probe will hybridize to its target sequence, to a detectably greater degree than other sequences (e.g. at least 2-fold over background). Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH at which 50% of a complementary target sequence hybridizes to a perfectly matched probe. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C. Hybridization procedures are well-known in the art and are described in Ausubel et al., (Ausubel F. M., et al., 1994, Current Protocols in Molecular Biology, John Wiley & Sons Inc.).

"Isolated" refers to material that is: (1) substantially or essentially free from components which normally accompany or interact with it as found in its naturally occurring environment; or (2) if in its natural environment, the material has been non-naturally altered to a composition and/or placed at a locus in the cell not native to a material found in that environment. The isolated material optionally comprises material not found with the material in its natural environment. For example, a naturally occurring nucleic acid becomes an isolated nucleic acid if it is altered, or if it is transcribed from DNA which is altered, by non-natural, synthetic methods performed within the cell from which it originates.

Two DNA sequences are "operably linked" if the linkage allows the two sequences to carry out their normal functions relative to each other. For instance, a promoter region would be operably linked to a coding sequence if the promoter were capable of effecting transcription of that coding sequence and said coding sequence encoded a product intended to be expressed in response to the activity of the promoter.

A "polynucleotide" is a sequence of two or more deoxyribonucleotides (in DNA) or ribonucleotides (in RNA).

A "DNA construct" is a nucleic acid molecule that is isolated from a naturally occurring gene or which has been modified to contain segments of nucleic acid which are combined and juxtaposed in a manner which would not normally otherwise exist in nature.

A "polypeptide" is a sequence of two or more amino acids.

A "promoter" or transcriptional regulatory region is a cis-acting DNA sequence, generally located upstream of the initiation site of a gene, to which RNA polymerase may bind and initiate correct transcription.

A "recombinant" polynucleotide, for instance a recombinant DNA molecule, is a novel nucleic acid sequence formed through the ligation of two or more nonhomologous DNA molecules (for example a recombinant plasmid containing one or more inserts of foreign DNA cloned into it).

"Stress tolerance" refers to any type of stress that a plant may have to endure, and the capacity of such plant to tolerate the stress. The stress may be selected from a group including, but not limited to, heat, cold, frost, drought, flood, high winds etc. The stress may also be induced by other external factors including pest infestation and plant disease. Therefore the term "stress" further encompasses such insults. Stress tolerance relates to the capacity of a plant to cope with any such stresses without excessive damage and/or death.

"Growth potential" refers to the present and future ability of a plant to exhibit increased growth or vigor. Such growth may pertain to the entire biomass of the plant, but may also relate to the growth of specific organs. Increased growth or vigor relates to the rate at which a particular plant or plant organ changes weight. Typically such change in weight will be a gain in weight, but in certain in circumstances may also pertain to a loss in weight where desirable.

"Transformation" means the directed modification of the genome of a cell by the external application of recombinant DNA from another cell of different genotype, leading to its uptake and integration into the subject cell's genome.

A "transgenic plant" encompasses all descendants, hybrids, and crosses thereof, whether reproduced sexually or asexually, and which continue to harbour the foreign DNA.

DETAILED DESCRIPTION OF THE PREFERRED EMBODIMENTS

The present invention pertains to systems and methods for enhancing the capacity of a plant to respond to adverse abiotic conditions such as drought, salt and extreme temperatures. The invention also pertains to systems and methods for altering the growth characteristics and/or the lipid content of a plant. For this purpose, the systems and methods of the present invention harness known stress response metabolic pathways involved in the opening and closing of stomata. These pathways include those involved in the metabolism of plant cyclitols in relation to phytic acid biosynthesis for signal perception of environmental stresses. In this regard the present invention constitutes a segment of a more comprehensive program involving carbohydrate signal molecules and their influence upon plant performance. Unexpectedly, the inventors have discovered that these pathways can be dramatically enhanced by the overexpression of phosphoinositide-specific phospholipase C (PI-PLC). Although PI-PLC is known to be involved in stress-response pathways to close stomata, it would appear that the response of the plant is not optimal, and significantly greater response rates can be achieved when PI-PLC is overexpressed in guard cells.

PI-PLC plays a central role in the PI-specific signal transduction pathway. It catalyzes the hydrolysis of PIP2 to produce two second messengers, inositol 1,4,5-trisphosphate ($IP_3$) and diacylglycerol (DAG) (FIG. 1). The latter promotes the translocation of protein kinase C to the ER membrane, which, through phosphorylation, activates various proteins and enzymes. $IP_3$, on the other hand, is a cytosolic $Ca^{2+}$ modulator, which participates in protein activation and regulation of gene expression of various pathways as necessary.

The supply of $IP_3$ to the cell is stimulus-dependent and the molecule is short lived. Its removal from the system could be achieved either by de-phosphorylation to a lower phosphate-containing—or by further phosphorylation to a higher phosphate-containing inositol. Higher inositol phosphates include $IP_4$, $IP_5$ and $IP_6$ (phytic acid, PA). Although the biosynthesis of PA, through sequential phosphorylation of myo-inositol, is well documented (Stephens and Irvine, 1990; Brearley and Hanke, 1996; Yoshida et al., 1999; Loewus and Murthy, 2000), we are not aware of any established examples where PI-PLC provides an alternate pathway to PA accumulation in seeds of higher plants. However, $IP_3$ was shown to be further phosphorylated to form PA in *Saccharomyces cerevisiae* (York et al., 1999) and *Scihizosaccharomyces pombe* (Ongusaha et al., 1998).

To investigate the possible contribution of PI-PLC as an alternate pathway to PA accumulation and to examine the effect of up- and down-regulation of this enzyme on the general performance and seed characteristics of canola plants, we isolated the corresponding full-length cDNA encoding PI-PLC from *B. napus* (Accession # AF108123; Das et al., unpublished results) and constitutively expressed it in both orientations in canola using the CaMV35S promoter.

FIG. 1 provides schematic indication of some of the pathways and factors involved in the induction of a plant stress response to close stomata, and reduce water loss. PI-PLC is involved in the hydrolysis of phosphatidylinolsitol-4,5-biphosphate (PIP2) to inositol-1,4,5-triphosphate ($IP_3$) and diacylglycerol (DAG). Stress signals such as salt, drought or cold are perceived by the receptor and the G protein complex, which induces PI-PLC to hydrolyze PIP2 to IP3 and DAG. Both IP3 and DAG are involved in the signal transduction of the external abiotic signal into an intracellular response (e.g. stress response). It is noteworthy that most of the genes including PI-PLC of this pathway are induced by abiotic stress.

The inventors have succeeded in isolating several genes encoding products involved in this pathways, including PI-PLC from *Brassica napus*. The DNA sequence information for this gene is provided in SEQ ID NO: 3 of the sequence listing, and the corresponding peptide sequence as SEQ ID NO: 4 of the sequence listing. Moreover, the inventors have successfully expressed a recombinant version of this gene in *Brassica* by *Agrobacterium*-mediated transformation (see Examples). These plants overexpressed the PLC gene under the influence of the constitutive promoter CaMV35S. Under controlled growing conditions, over-expression of this enzyme in canola led to early bolting, flowering and podding and maturation in transgenic plants. Wild-type control plants lagged behind and matured almost 7-10 days later. The ramification of this finding would be a shorter growing season, which will be desirable in certain areas where an early frost would be detrimental to the overall yield. Furthermore, these transgenic plants were shown to be drought tolerant compared to the control plants when grown under severe drought conditions.

The invention encompasses the targeting of PI-PLC to the guard cells of the transformed plants. The guard cell volume can be manipulated by altering the turgor of the cell using PI-PLC as a mediator during drought stress to shrink the volume of the guard cell in order to reduce the water loss. As shown in the Examples, shrinking stimulus such as drought, for example, will activate PI-PLC mediated production of $IP_3$ leading to elevated $Ca^{2+}$ levels which inhibit $K^+$ channels and resulting cell shrinking. On the other hand, activation of PLA-mediated production of free acids will lead to activation of $K^+$ channels to restore the cell swelling when the stress is over.

The PI-PLC gene from *Brassica napus* was cloned in a plant transformation vector (see Examples.). This recombinant version of the gene was expressed successfully in transgenic plants (*Brassica napus* cv Westar).

Under controlled growing conditions, over-expression of this gene in canola led to early bolting, flowering and podding and maturation in transgenic plants. Wild-type control plants lagged behind and matured almost 7-10 days later (see Examples). A ramification of this finding is a shorter growing season, which will be desirable in certain areas where an early frost would be detrimental to the overall yield.

To test that over-expression of PI-PLC may accumulate higher level of phytic acid in the seeds, phytic acid was estimated in transgenic seeds. The results showed that transgenic seeds contain approximately 20% more phytic acid than the control plants (see Examples). This finding suggests that over-expression of PI-PLC has increased the flux through this pathway generating $IP_3$ as an intermediate which is subsequently phosphorylated to synthesize phytic acid.

The drought tolerance trait of the transgenics was also tested under controlled drought conditions. Both transgenics and control plants were grown under normal conditions initially. The growing plants were then subjected to drought by abstaining them from water for more than 3 weeks. At this time both transgenic and control plants looked severely affected by drought (see Examples). Subsequently, the plants were supplied with very limited amount of water. In 24 hours, only transgenic plant recovered but not the control plants. This experiment was repeated with a large number of plants. Results were similar.

This dramatic recovery of the transgenic plants strongly suggests that over-expressed PI-PLC has successfully, mediated the formation the necessary signaling elements for drought tolerance.

Full details of the aforementioned experimental results are provided in the Examples.

In addition to being a key component in the $PIP_2$ signaling pathway, and by virtue of its phosphorylation state, $IP_3$ provides a likely midway starting point towards the synthesis of $IP_6$. Earlier studies have shown this to be true in the case of lower eukaryotes such as yeast (York et al., 1999; Ongusaha et al., 1998). Assuming this to be true in higher plants, we surmised that constitutive production of $IP_3$ in developing seeds, by over expression of PI-PLC might lead to increased $IP_6$ accumulation. The results shown in Table 2 from transgenic *B. napus* plants seem to support this hypothesis. Thus, in comparison to wild type, transgenic plants accumulated 20% more of seed $IP_6$ (which parallel the observed increase in $IP_3$). In contrast, transgenic plants expressing the PI-PLC gene in antisense orientation did not show any changes in seed $IP_6$ levels in either direction. This indicates that $PIP_2$ hydrolysis is not a primary substrate source for PA biosynthesis, but rather a secondary pathway whose role may be limited to feed back type of responses. Since this is not a conclusive evidence of PI-PLC being the main cause for the higher levels of seed phytic acid, further experiments such as measurement of $IP_3$ in the developing seeds, need to be done to establish their direct relationship.

Some recent reports also suggest that longer-term increase in $IP_3$ is associated with plant cell growth in tobacco in tobacco (Kost et al., 1993), *Papaver*(Franklin-Tong et al., 1996) and maize (Perera et al., 1999; Stevension et al., 2000). The source for the $IP_3$ in this case is $PIP_2$, which is hydrolyzed by PI-PLC.

Over-Expression of PI-PLC Alters the Growth Pattern in *Brassica napus:*

Sustained increase in transient levels of $IP_3$ appears to be associated with plant cell growth (Elizabeth Rosen, Rujin Chen and Patrick H. Masson. *Trends Plant Sci.* 4 (1999), pp. 407-412).

*B. napus* requires at least 90-100 days to complete its life cycle which is not short enough to avoid cold stress during seedling stage and early-frost damage during or before harvest.

On the other hand, the early bolting and maturity exhibited by transgenic plants, over-expressing PI-PLC. The inventors have shown that plants grew normal and at equal growth rate until bolting when an accelerated growth was observed in the transgenics which showed the stem elongation followed by early bolting and maturity for the transgenics. The early bolting and maturity is very significant because this will shorten the life cycle of the plant thus will be able to avoid the frost damage during harvest.

Although we do not know the molecular mechanism for this change, we have speculated a few. First, the over-expression of PLC possibly has resulted in increased supply messenger compounds which, in turn, released and activated $Ca^{2+}$ and calmodulin-dependent proteins, protein kinases and other proteins including ion channels, receptors, transporters, cytoskeletal components and growth regulators. Indeed, evidence exists that PI-PLC mediated signal transduction pathway is involved in cell growth and development as observed in tip-growing cells (Kost et al. 1993; Franklin-Tong et al., 1996) and in gravistimulated maize pulvini (Perera et al., 1999; Stevenson et al., 2000). Works in maize, for example, showed that sustained IP3 increase was related to increased IAA levels and altered carbohydrate metabolism through higher invertase activity in the gravistimulated pulvini (Stevens et al., 2000). It is known in many actively growing tissues undergoing expansion, invertase activities are found to be high (Morris 1982; Morris and Arthur, 1984). Based on this report we measured the IAA levels in the transgenic plants.

Over-Expression of PI-PLC Resulted in Increased Phytic Acid Level and Higher Oil Content in Transonic *B. napus:*

As mentioned in FIG. 1, it is proposed that $IP_3$ produced from the hydrolysis of PIP2 can be further phosphorylated to polyphosphate inositol such as phytic acid. The inventors have demonstrated for the first time that over-expression of PI-PLC could lead to increased flux through this pathway resulting in increased phytic acid. Although this correlative observation suggests that over-expression is the causal factor for the increased level of phytic acid, further works, such as measurement of $IP_3$ in the developing seeds, need to be done to establish their direct relationship.

Figure 9:
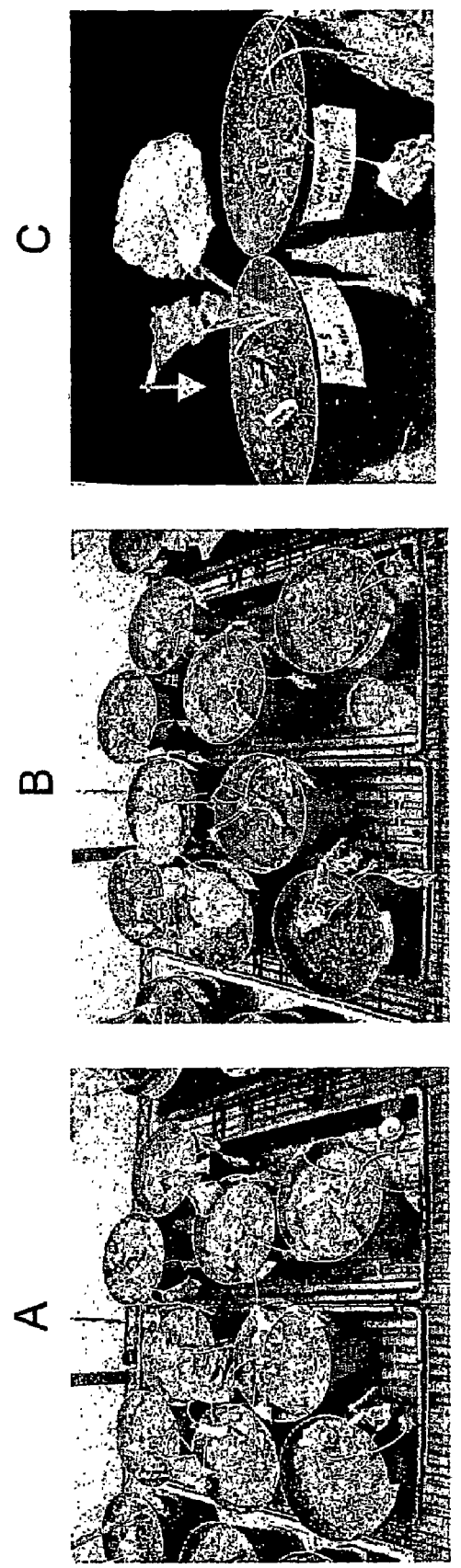
FIG. 9 provides a comparison of transgenic and control plants under drought stress. Panel A, plants after 24 days of drought. Panel B and C after limited rewatering. Arrow points to transgenic drought survivor.

As shown in FIG. 1, hydrolysis of PIP2 by PI-PLC results in IP3 and DAG. In animals, the latter is involved in activation of protein kinase C (PKC). However, a very few reports are available in plants to shows that DAG is associated with the activation of PKC (Namori et al., 1994). Although a few other reports showed the presence of PKC in plants as defense response (Subramaniam et al., 1997; Roux et al., 1996), we still lack consensus evidence that DAG is an intracellular messenger in plants, as demonstrated in animals (Miege and Marechal, 1999). In plants, DAG is the most basic ingredient for cell membrane biogenesis as well as for fat storage. It is placed at a strategically interesting step in the metabolism of lipids: it can either go for membrane biogenesis or can be further acylated for oil biosynthesis as observed in oilseed crops such as *Brassica napus*. One biologically important feature should be mentioned here is that, the proportion of certain acyl groups (fatty acids) present in DAG molecules derived from signal transduction pathway are some what different than the proportion of those acyl groups present in the DAG that participate in oil biosynthesis. In our present study with *Brassica napus*, we observed increased level of oil in the seeds from transgenic plants over-expressing PI-PLC. Since PI-PLC generates DAG as a co-product after hydrolysis of PIP2, we investigated the fatty acid profile of the oil. As shown in FIG. 9, increased oil is contributed by 18:X (number denotes the # of carbons in the fatty acid chain, while X denotes # of double bonds in the same). Although it is possible that these extra 18:X species can be added to the oil via the normal Kennedy pathway, it is not unlikely that these fatty acid species may also come from DAG derived from the hydrolysis of PIP2. It has been reported in the studies that used pea leaf, potato tuber and soy-beans showed, phosphatidylinositol (PI), the upstream precursor for PIP2 and DAG, contain 18:X (18:0/18:2 18:0/18:3 and 18:0/18:1) as a major component. A recent report also showed that a maize mutant exhibiting increased PI content in the kernel contained higher triacylglycerol (oil) accumulation in the endosperm (Shank et al., 2001). It is interesting to note that oil is generally accumulated in the maize embryos and not in the endosperm, which generally contributes very little to oil accumulation actually contained higher oil. Commonly, all plant species that accumulate oil follow the Kennedy pathway i.e. sequential acylation of glycerol-3-P molecule by fatty acids to biosynthesize oil. In this case, DAG (derived from PIs) appears to have contributed directly to oil accumulation. Therefore, the inventors propose that oil accumulation in oilseeds can occur via Kennedy pathway as well PI-metabolic pathway.

Over-Expression of PLC in *B. napus* Showed Increased Tolerance to Drought:

In order to see the effect of over-expression of PLC on drought tolerance in *B. napus*, both transgenics and control plants were subject to water deprivation for 24 days. After 24 days of drought 1st 100 mL water was applied to all the plants. One transgenic plant recovered the drought after 1st watering. The other +ve and control plants did not recover the drought even after normal watering was resumed (see Examples).

Based on this result, the physiological and molecular bases are sought to explain such a dramatic recovery of the transgenics. The following attempts were taken to explain the basis of the recovery.

The transgenic plants over-expressing PLC should produce elevated levels of $IP_3$ which may have triggered the changes in $Ca^{2+}$ level thereby regulating $Ca^{2+}$ and calmodulin-dependent enzymes and channels. The other product of the hydrolysis of PIP2 is diacylglycerol (DAG) which remains in the membrane and activates protein kinase C (PKC) which, through phosphorylation, modulates variety of proteins. Thus rapid changes in $IP_3$ in transgenics could be an "all purpose wake-up call" for the plants under drought stress after rewatering. It is possible that necessary proteins and/or other compounds built up in the transgenics during the drought period were not exhausted even after 24 days of drought. As soon as water became available, the "all purpose wake up call" comprised of possibly stable membrane structures and functions, and/or accumulated induced proteins protecting the membranes and other cell constituents become functional. One of the possibilities is that special enzymes have been induced thereby scavenging free radicals, the compounds that accumulate under water stress and disrupt the structural and functional integrity of the cell membranes.

Figure 8:
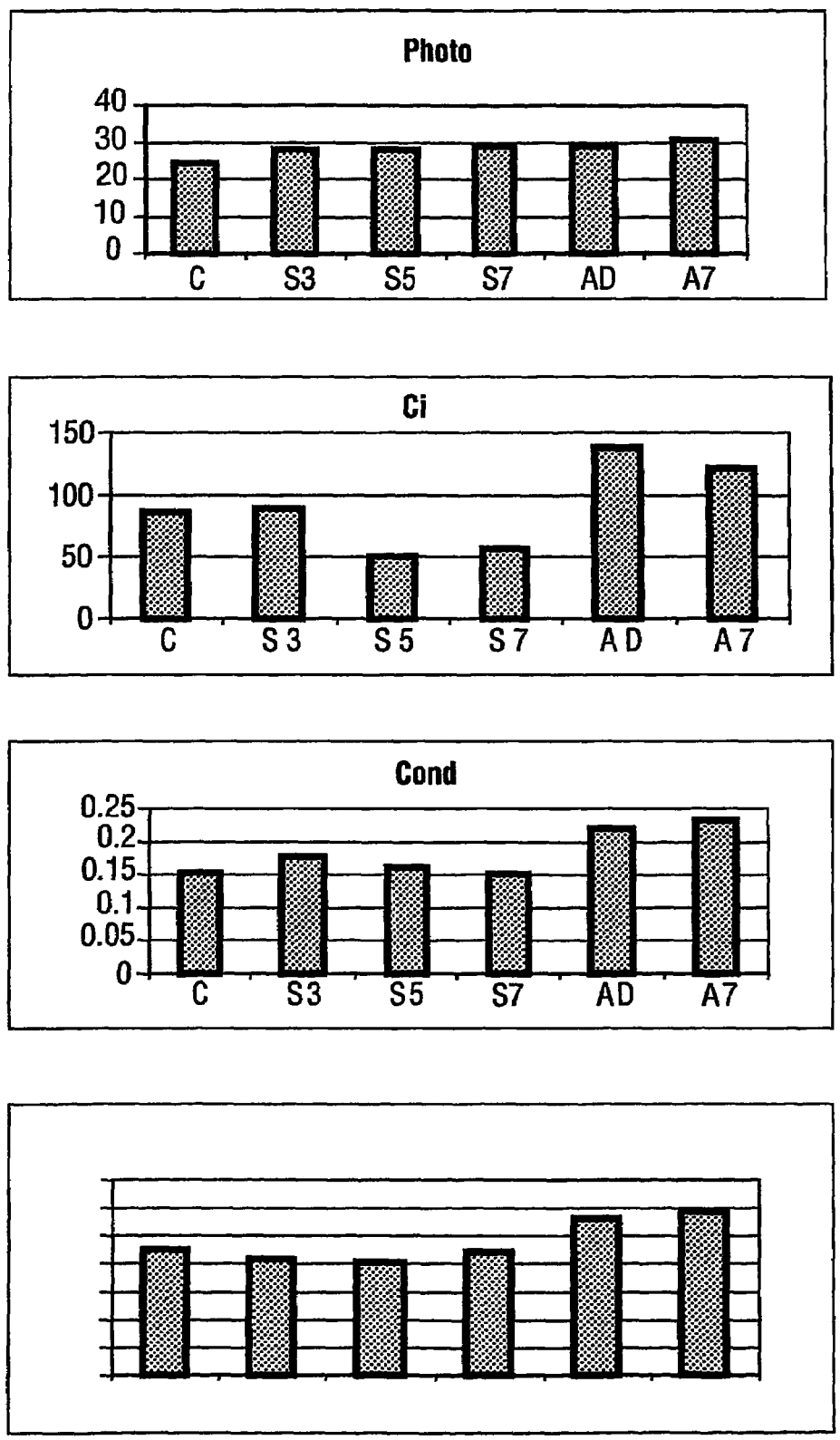
FIG. 8 Photosynthesis (Photo), Intercellular carbon dioxide (Ci) Conductance to water (Con) and transpiration (Trmmol) of *Brassica napus* control (C), overexpressed (S) and antisense (A) plants grown under controlled conditions (see Examples).

It is also possible that during drought stress, the transgenic plants that recovered from the drought have maintained a low level of water due to reduced water loss via some means. Over-expression of PLC may have induced the reduction in stomatal aperture upon dehydration to reduce the water loss. Substantial evidence is available in the literature, which reported that PI-specific signal transduction is involved in opening and closing the stomata via second messengers produced by PLC. Measuring photosynthetic capacity and water movement through stomata would reveal the effect of altered PLC activity on these physiological parameters. In order to test this hypothesis, the inventors measured the transpiration rate, internal $CO_2$ conc., water conductivity and photosynthesis of the transgenic plants over-expressing PI-PLC. FIG. 8 shows that transpiration rate and internal CO2 conc. in some transgenics are lower than the control plants. Although we do not have any guard cell data, this result, implicates that over-expression of PI-PLC may have altered the guard cell pore and regulated the transpiration rate and the conc. of CO2 in the cell.

A few recently published works showed phosphatidic acid as an emerging plant lipid second messenger in that it is a product of two signaling pathways, those of phospholipase C and D, the former in combination with diacylglycerol kinase (Frank et al., 2000; Munnik et al., 2000). In a recent review article, Munnik et al, (2001) proposed that both PLC and PLD are involved in signal transduction, and phosphatidic acid (PA) and diacylglycerol pyrophosphate (DGPP) obtained from both PLC and PLD pathways are the emerging second messengers. We mentioned earlier that DAG is precursor for both membrane as well storage lipids and a very few reports are available to suggest that DAG per se is directly involved in signal transduction in plants. Munnik et al., proposed that DAG produced through hydrolysis of PIP2 is converted to PA and DGPP instead of activating the PKC as in the case of animals. While DAG contributed to the oil content in the transgenic seeds, DAG may have been converted to DGPP in the transgenic plants under stress in this case. Future works of this line are needed to test these hypotheses.

The expression constructs that are used in the systems and methods of the present invention comprise various DNA sequences ligated together. To generate these constructs, standard ligation techniques that are well known in the art may be used. Such techniques are readily obtainable from any standard textbook relating to protocols in molecular biology, and suitable ligase enzymes are commercially available.

In another embodiment of the present invention, recombinant DNA construct so expressed may be engineered to express an altered form of the wild-type PI-PLC protein, or engineered to reduce the expression of the wild-type gene.

Importantly, any gene encoding a PI-PLC Method for the identification and isolation of homologous DNA sequences are very well known in the art and are included, for example in Sambrook et al., *Molecular Cloning: A Laboratory Manual*, Cold Spring Harbour Press, Cold Spring Harbour, N.Y. (1989). For example, a nucleotide sequence encoding a PI-PLC can be utilized to design oligonucleotide probes. The probes can be labelled (e.g. radiolabelled) and used to screen cDNA or genomic DNA libraries of other plant species for DNA sequences that are homologous to PI-PLC. As is well known in the art, the hybridization conditions of DNA library screening can determine the degree of specificity of homologous sequence annealing and recognition. For example, conditions of high stringency will identify only those DNA sequences more closely related to PI-PLC, whereas conditions of lower stringency will identify further DNA sequences that have less homology to PI-PLC. In any event, PI-PLC sequences can be identified for use with the systems and methods of the present invention.

In another embodiment of the invention, the nucleotide sequences encoding PI-PLC may also be used for the identification of related homologous sequences deposited in public databases through comparative techniques well-known in the art. This may permit the identification of related cDNA or genomic sequences from various species, including plant species, where the DNA sequence information for PI-PLCs is not known. In particular it is contemplated that these sequences so described can be used for the isolation of plant genes encoding similar activities.

Further, it is apparent to one skilled in the art that the polynucleotide and deduced amino acid sequences of PI-PLC enzymes can be used to isolate related genes from various other plant species. The similarity or identity of two polypeptide or polynucleotide sequences is determined by comparing sequences. In the art, this is typically accomplished by alignment of the amino acid or nucleotide sequences and observing the strings of residues that match. The identity or similarity of sequences can be calculated by known means including, but not limited to, those described in *Computational Molecular Biology*, Lesk A. M., ed., Oxford University Press, New York, 1988, *Biocomputing: Informatics and genome Projects*, Smith, D. W., ed., Academic Press, New York, 1993., *Computer Analysis of Sequence Data. Part I*, Griffin, A. M. and Griffin, H. G., eds., Humana Press, New Jersey, 1994 and other protocols known to those skilled in the art. Moreover, programs to determine relatedness or identity are codified in publicly available programs. One of the more popular programs comprises a suite of BLAST programs, three designed for nucleic acid sequences (BLASTN, BLASTX and TBLASTX), and two designed for protein sequences (BLASTP and TBLASTN) (Coulson, Trends in Biotechnology, 12:76-80, 1994). The BLASTX program is publicly available from NCBI and other sources such as the BLAST Manual, Altschul, S., et al., NCBI NLM NIH Bethesda Md. 20984, also www.ncbi.nlm.nih.gov/BLAST/blast help provides online help and further literature references for BLAST and related protein analysis methods, and Atschul, S., et al., J. Mol. Biol 215:403-410, 1990.

The isolated polynucleotide can be sequenced and the DNA sequence used to further screen DNA sequence collections to identify related sequences from other species. The DNA sequence collections can comprise EST sequences, genomic sequences or complete cDNA sequences.

It will also be understood to a person of skill in the art that site-directed mutagenesis techniques are readily applicable to the polynucleotide sequences of the present invention, to make the sequences better suited for use in generated morphologically modified transgenic plants. Related techniques are well understood in the art, for example as provided in Sambrook et al., *Molecular Cloning: A Laboratory Manual*, Cold Spring Harbour Press, Cold Spring Harbour, N.Y. (1989). In this regard, the present invention teaches the use of nucleotide sequences derived from wild-type PI-PLC genes. However, the present invention is not intended to be limited to these specific sequences. Numerous directed mutagenesis techniques would permit the non-informed technician to alter one or more residues in the nucleotide sequences, thus changing the subsequently expressed polypeptide sequences. Moreover, commercial 'kits' are available from numerous companies that permit directed mutagenesis to be carried out (available for example from Promega and Biorad). These include the use of plasmids with altered antibiotic resistance, uracil incorporation and PCR techniques to generate the desired mutation. The mutations generated may include point mutations, insertions, deletions and truncations as required. The present invention is therefore intended to encompass the use of corresponding mutants of PI-PLC genes, relating to both cDNA and genomic DNA sequences in accordance with the teachings of the present application.

Additional mutagenesis techniques permit the generation of modified PI-PLC genes encoding PI-PLC proteins with truncations and deletions. Typically, techniques for generating such truncated and deleted forms of PI-PLC proteins may involve polymerase chain reaction. The expression of PI-PLC peptides exhibiting truncations and deletions may confer favourable properties to the systems and methods of the present invention, and it is the intention of the invention to encompass all such methods and systems that employ expression constructs encoding PI-PLC proteins harbouring useful truncations and deletions.

The expression of the PI-PLC protein may occur via any one of numerous suitable promoter sequences. Preferably, the promoter is a relatively strong promoter that indices overexpression of the PI-PLC protein. More preferably, the promoter is inducible such that expression of the PI-PLC protein is switched on when the plant cell or plant is exposed to adverse conditions or stress, such as low water. Most preferably, the promoter is specific for expression of PI-PLC within the guard cells of the plant. In this way, the selective expression of PI-PLC directs targeting of the exogenously expressed protein to the guard cells, without substantially effecting the remainder of the plant. Under specific circumstances it may be desirable to use a promoter having constitutive activity to drive continuous PI-PLC expression regardless of conditions. Many suitable promoter sequences are known to those skilled in the art. However, the present invention defines for the first time a promoter sequence specifically directs gene expression within guard cells.

The use of gene inhibition technologies such as antisense RNA or co-suppression or double stranded RNA interference is within the scope of the present invention. In these approaches, the isolated gene sequence is operably linked to a suitable regulatory element.

Accordingly, in one embodiment of the invention the subject method includes a method to modify the stress response or growth potential of a plant comprising the steps of:
   a.) Introducing into a plant cell capable of being transformed a genetic construct comprising a first DNA expression cassette that comprises, in addition to the DNA sequences required for transformation and selection in said cells, a DNA sequence that encodes a PI-PLC enzyme, at least a portion of said DNA sequence in an antisense orientation relative to the normal presentation to the transcriptional regulatory region, operably linked to a suitable transcriptional regulatory region such that said recombinant DNA construct expresses an antisense RNA or portion thereof of an antisense RNA and,
   b.) recovery of a plant which contains said DNA sequence.

It is apparent to the skilled artisan that the polynucleotide encoding the PI-PLC sequence can be in the antisense (for inhibition by antisense RNA) or sense (for inhibition by co-suppression) orientation, relative to the transcriptional regulatory region. Alternatively a combination of sense and antisense RNA expression can be utilized to induce double stranded RNA interference (Chuang and Meyerowitz, PNAS 97: 4985-4990, 2000, Smith et al., Nature 407: 319-320, 2000).

These methods and the correspondingly generated transgenic plants rely on the use of transformation techniques to introduce the gene or construct encoding PI-PLC (or a part or a homologue thereof) into plant cells. Transformation of a plant cell can be accomplished by a variety of different means. Methods that have general utility include *Agrobacterium* based systems, using either binary and/or cointegrate plasmids of both *A. tumifaciens* and *A. rhyzogenies*. (e.g., U.S. Pat. No. 4,940,838, U.S. Pat. No. 5,464,763), the biolistic approach (e.g, U.S. Pat. No. 4,945,050, U.S. Pat. No. 5,015,580, U.S. Pat. No. 5,149,655), microinjection, (e.g., U.S. Pat. No. 4,743,548), direct DNA uptake by protoplasts, (e.g., U.S. Pat. No. 5,231,019, U.S. Pat. No. 5,453,367) or needle-like whiskers (e.g., U.S. Pat. No. 5,302,523). Any method for the introduction of foreign DNA and/or genetic transformation of a plant cell may be used within the context of the present invention.

The following examples serve to illustrate the method and in no way limit the utility of the invention.

EXAMPLES

Example 1

Isolation of RNA from *B. napus*

RNA was isolated from germinated seeds (3 days old germinated seeds on moistened filter paper in a Petri plate in the dark) using Plant RNA Miniprep method (according to RNeasy Plant handbook for RNA minipreps, 1995). Briefly, the samples were ground to fine powder with mortar and pestle. The ground samples in the microcentrifuge tubes containing lysis buffer were vortexed and spun onto a shredding column for 2 min. Ethanol was added to the flow-through and transferred to a spin column and spun. The column containing RNAs were washed twice with the washing buffer. Finally, RNA was eluted with DEPC-treated water to a new centrifuge tube. The elute containing the total RNA was stored at –70° C. until used.

Example 2

Primer Design and PCR Amplification of the Full Length PI-PLC cDNA

Primers were designed using the heterologous (*Arabidopsis*) PI-PLC-specific ORF (Hirayama et al., 1997). The forward primer was designed from the 5' end including the start codon, and the reverse primer from the 3' end, which included the stop codon. The primers used were: 5' CATGTCGAAG-CAAACGTACAAAGT 3' (SEQ ID NO: 1) and 5' ACA-CAAACTCCACCTTCACGAGAA 3' (SEQ ID NO: 2). Primers were synthesized in our lab in a DNA synthesizer (Applied Biosystems, 392 DNA/RNA synthesizer) and used to amplify the $1^{st}$ strand cDNA synthesized from mRNA of the *Brassica napus* germinated seeds using 1st strand cDNA synthesis kit (Boehringer and Mannheim). An aliquot (5 μL) of the reaction mixture was run in an agarose gel and, as expected, a 1.7 Kb fragment was recovered.

Example 3

DNA Sequencing

A series of primers were designed and used to sequence the PCR-amplified cDNA fragment. Subsequently, the fragment was identified as PI-PLC gene involved in signal transduction and submitted to the GenBank (Accession # AF108123). The gene, as expected, has more than 90% sequence similarity to *Arabidopsis* PLC gene and very high amino acid sequence similarity to many other plant PLC sequences.

Example 4

Plant Transformation

Figure 3:
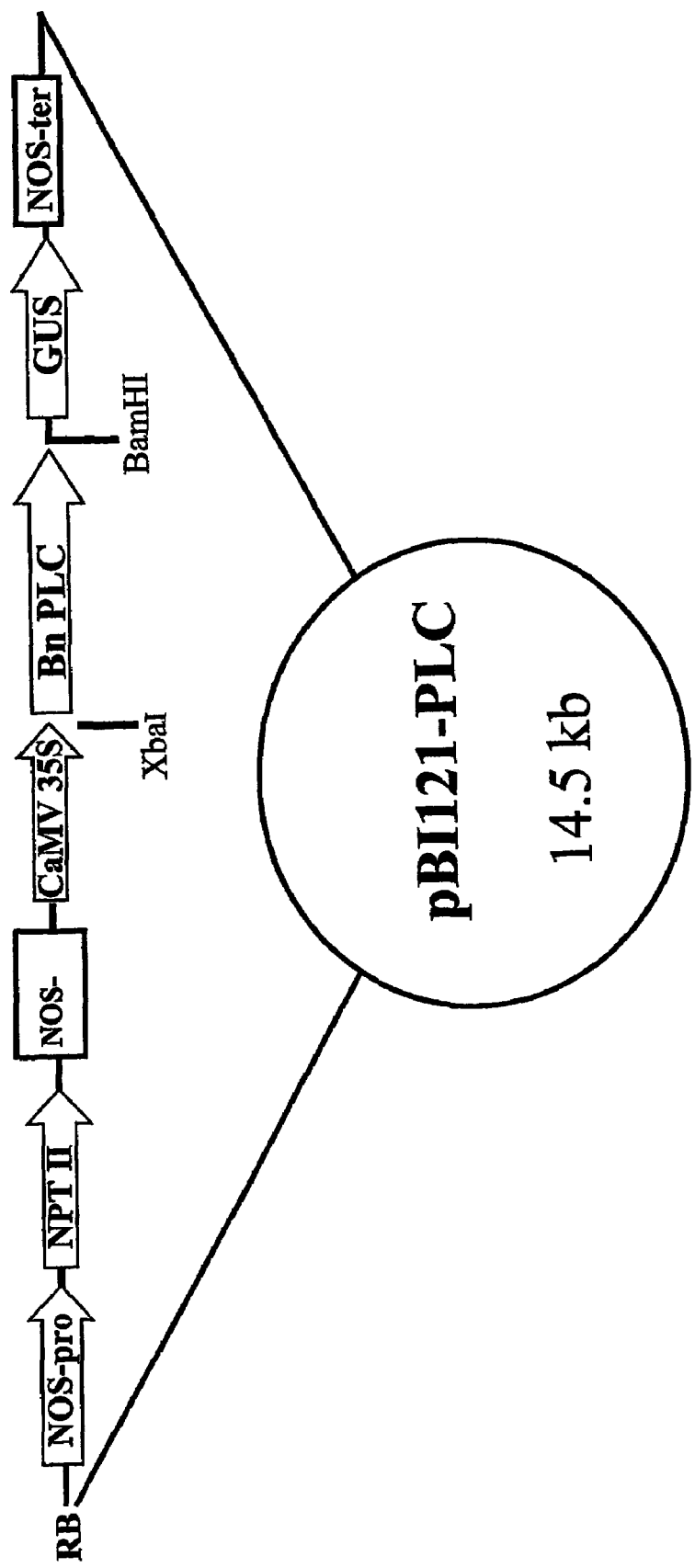
FIG. 3 schematically illustrates the pBI121-PLC expression construct designed for use with the systems and methods of the present invention.

The PI-PLC cDNA was cloned between XbaI and BamHI sites in the plant vector pBI121 (see FIG. 3). *Agrobacterium*-mediated transformation was done using cotyledonary petioles, following the method of Moloney et al., 1989. Transgenic plants were screened routinely by PCR amplification using vector-based primers. Gene expression was verified through positive GUS assays, both in situ and in vitro gel assays. Transgenic plants containing a single copy of the insert, as determined by Southern hybridization, were selected for seeds. Primary transformants were transferred into soil and a back up of each plant was kept in jars for future use. Plants were grown under 16 h light/8 h dark with temperature of 20° C./15° C. respectively, and were watered normally. Homozygosity was achieved at the $4^{th}$-generation, whose seeds were harvested and used in subsequent experiments.

Example 5

Phytic Acid Calorimetric Analysis

Approximately 30 seeds from each line were sorted and ground to a fine powder. Three replicates of 3.5-4.0 mg seed powder were weighed out and 40 μl/mg of 0.5N $HNO_3$ was added. Samples were vortexed briefly and incubated for 1 hour at room temperature while shaking. Samples were vortexed again and centrifuged at 4000 g for 2 minutes. Immediately following centrifugation, 40 μl of the supernatant was promptly removed. 5 μl of the supernatant was mixed with 187 μl of calorimetric reagent solution #1 in duplicates (10 μl ferric ammoniumsulfate, 95 μl 0.5N $HNO_3$, and 82 μl dd. $H_2O$). Solutions were heated for 1 minute at 94° C. After cooling, 8 μl of solution #2 were added. Samples were mixed and transferred to a microtiter plate for reading at 450 nm in a kinetic microtiter plate reader. A standard curve was obtained by preparing a 4 μg/μl solution of phytic acid (sodium salt) in 0.5N $HNO_3$. 2, 4, 8, 10, 12, 14 and 16 μg of phytic solutions were prepared by adjusting the volume to 5 μl with 0.5N $HNO_3$. The samples were mixed with 187 μl of calorimetric solution #1 and heated at 95° C. for 1 minute and cooled at room temperature. 8 μl of solution #2 was added, the samples were mixed and transferred to a microtiter plate for reading at 450 nm in a microtiter plate reader as before. Reliability of the standard as a mean to predict unknown μg of phytic acid was determined by the linearity of the standard curve, plotting OD amounts against concentrations. The known concentrations and OD readings corresponding to the standards were used to determine the μgs of phytic acid in the samples.

Example 6

RNA Isolation and Northern Hybridization

RNeasy kit (QIAGEN) was used for RNA isolation from *B. napus* leaf material. Five-microgram samples of RNA were separated in a denaturing formamide-containing agarose gel, and the RNAs were transferred to Hibond-N membrane overnight. The RNAs were then crosslinked to the membrane using UV radiation. The membranes were probed with labeled PI-PLC gene and visualized by autoradiography.

Example 7

Protein Expression in *E. coli* and Production of Polyclonal Antibodies

The PI-PLC gene was cloned into the *E. coli* expression vector, pProEX HT, and expressed by induction with IPTG. Both native and denatured proteins were isolated and purified. The purified protein was used to raise polyclonal antibodies in rabbits.

Example 8

Western Analysis of Proteins from Transgenic Plants

Protein samples were extracted from both control and transgenic plants, run in an SDS-polyacrylamide gel and by blotted onto polyvinylidene difluoride (PVDF) membranes. These were subsequently probed with the polyclonal antibodies using the Immuno-Blot Assay kit. Primary antibodies bound to the membrane-immobilized proteins were detected with a secondary antibody coupled to alkaline phosphatase for a colour reaction.

Example 9

Plant Growth and Development

Both transgenic and control plants were grown in 6" pots containing Readyearth soil mix at 20/15° C. and 16/8 day/night cycle respectively. The plants were regularly watered. The growth parameters such as days to bolting and days to maturity were recorded.

Example 10

Drought Stress

Transgenic plants, over-expressing PI-PLC, as well as wild types were grown in 6" pots containing Readyearth soil mix. Plants were watered as required for 24 days, after which time watering was completely stopped and pots were allowed to dry up for the next 24 days. At the end of the designated drought period plants were re-watered at 100 ml of water per plant per day. Watering was continued for next 3 days at this rate. On the fourth day, normal watering was resumed and the performance of the plants was recorded.

Example 11

GUS Assays

Figure 4:
FIG. 4 provides and indication of GUS expression in a transgenic sense seedling plant (right) and a lack of expression in a control plant (left).
Figure 5:
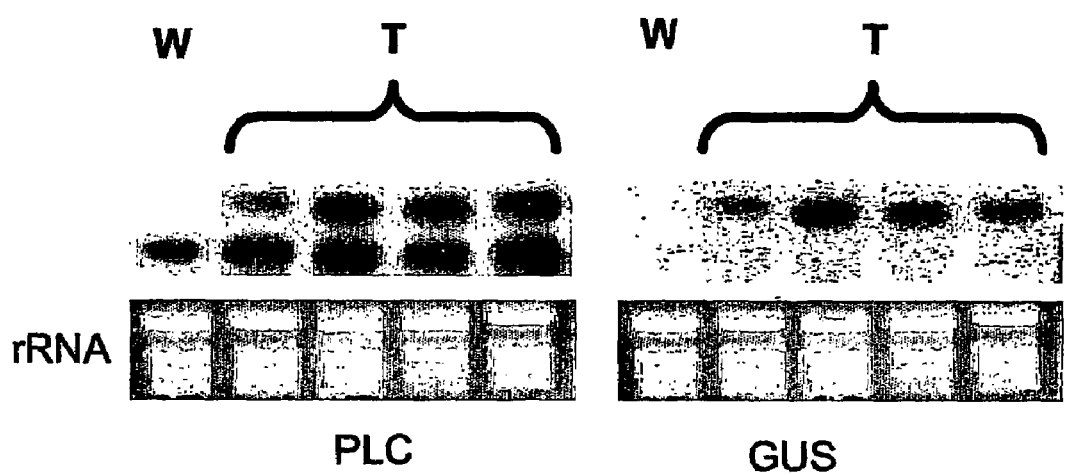
FIG. 5 provides Northern blots to illustrate the over-expression of the PLC gene in transgenic plants compared to control (W). The left panel was probed with PLC and the right panel with GUS gene.

Transgenic *B. napus* plants were monitored for GUS expression and activity both in planta (FIG. 4) as well as in vitro gel assay (FIG. 5). Both types of assays confirmed the presence of an active GUS enzyme in transgenic plants.

Example 12

Protein Expression, Purification and Antibody Production

BnPLC was expressed in ProEX HT Prokaryotic Expression System. The protein expressed was fused to a 6 histidine sequence $(his)_6$ for affinity purification. The purified protein was subsequently used to develop polyclonal antibodies.

Example 13

Over-Expression of PI-PLC in the Transgenic Plants

Northern analysis was done to study the transgenics overexpressing PLC (FIG. 5). FIG. 5 shows the initial transgenics that overexpressed the inserted PLC gene. As expected, two bands were observed in transgenics while the control showed only one band corresponding to the endogenous PLC. Both bands were detected using PLC gene as a probe, which could detect both endogenous as well as the inserted PLC. Since the upper band (representing the inserted gene) in the top row expected to have the GUS gene attached to PLC transcript, the membrane was stripped to remove the PLC probe and reprobed with GUS probe alone. As expected, a single band appeared for all the transgenics, and no band appeared at the corresponding spots which represent the endogenous PI-PLC. Also no band appeared in the control because the control plant does not contain the inserted gene fused to PLC.

The transgenic plants were allowed to self pollinate to produce F2 followed by F3 families. As expected, segregation of the PLC gene was observed in F2. In F3, however, inserted PLC attained homozygosity. These homozygous lines were used for growth, quality parameter assessment and drought experiments.

Example 14

Effect of Altered PLC Level on Growth and Development of Transgenics

Both transgenics and control seeds were planted in 6" pots containing Readyearth and the plants were raised and watered, as required, and observed for any change in growth habit. The data were collected for days to bolting, days to mature, # of branches/plant, and # of siliques/plant (see Table 1).

TABLE 1

Measurements of some physiological characters of the transgenic plants compared to the control

| Genotype | Days to bolt | Physiol. Maturity (days) | # of branches | # of siliques |
|---|---|---|---|---|
| Control | 41.6 ± 1.81 | 93.0 ± 2.00 | 3.6 | 34.0 |
| Trans. | 35.0 ± 1.56 | 85.1 ± 1.24 | 5.3 | 30.1 |

The data mentioned in Table 1 were taken from the plants grown under controlled growing conditions i.e. in a growth room. The parameters such as days to bolt and days to attain physiological maturity attained earlier in the transgenics compared to control. While transgenics have produced more branches compared to control, transgenics have less number of pods compared to control. However, the pods in most of the transgenics are bigger in size than the control (data not shown). The ultimate parameter such as yield is yet to be evaluated under both growth room as well as field conditions.

Figure 6A:
FIG. 6(a) provides a comparison of transgenic canola expressing PLC in a sense orientation (left), and antisense orientation (middle) and a control plant (right).
Figure 6B:
FIG. 6(b) provides a comparison of transgenic canola expressing PLC in a sense orientation (left), and antisense orientation (right).

With respect to early flowering, both transgenics and control plants grow at a normal rate during their initial vegetative growth. However, the transgenics started showing an accelerated growth just before the bolting resulting in early bolting and maturity (FIG. 6). In order to see if over-expression has altered the level of indole acetic acid (IAA) in the transgenic plants (see the discussion), IAA was measured from the samples comprised of the stems of the transgenic plants at their accelerated growth phase. However, no significant difference was observed (data not shown).

Example 15

Phytic Acid and Oil Content in the Transgenic *B. napus* Over-Expressing PLC

Figure 7:
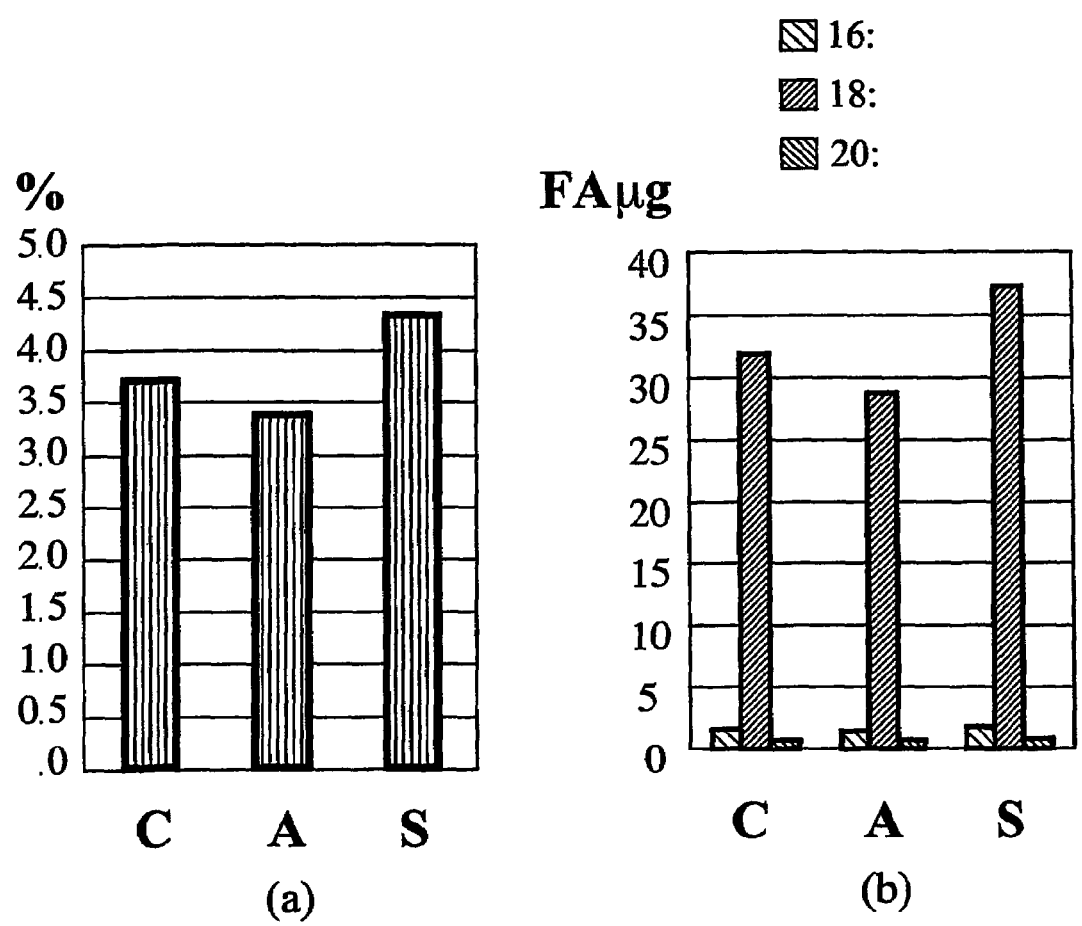
FIG. 7(a) percentage oil and (b) fatty acids in µg per mg DW) of *Brassica napus* control (C), overexpressed (S) and antisense (A) plants grown under controlled conditions (see Examples).

Both phytic acid and oil content were measured from the mature dry seed. As expected, phytic acid content was higher (ca. 20%) in the transgenics compared to the control plants, both of which were grown in controlled conditions as described earlier. Surprisingly, oil content was increased in the transgenic seeds. Since it is assumed that oil content increase was due to the contribution from DAG after hydrolysis of PIP2 during signal transduction, we investigated the fatty acid profile of the oil. As shown in the FIG. 7, increased oil is contributed by 18:X fatty acids which are the acyl groups found in PIs in different plant tissues (see discussion).

TABLE 2

Phytic Acid in Transgenics Over-expressing PLC Gene In *Brassica napus* (n > 5 ± SE)

| Genotypes | Mean ± SE |
|---|---|
| Control | 7.34 ± 0.41 (n = 5) |
| Transgenics | 9.07 ± 0.28 (n = 17) |

Example 16

Photosynthesis, Intercellular Carbon Dioxide Concentration, Water Conductance and Transpiration In order to study the effect of over expression of PLC on physiological parameters such as photosynthetic capacity (Photo), intercellular carbon dioxide (C), water conductivity (Cond) and transpiration rates (Tmml) plants were grown normally and measured these parameters. FIG. 8 shows that transpiration rate and internal CO2 conc. in some transgenics were lower than the control plants. However, no difference was observed with respect to water conductivity rate and photosynthesis capacity between the transgenics and the control (FIG. 8). Although antisense plants had higher C, Cond, Tmml, compared to sense and control plants, photo was not different.

Example 17

Effect of Drought on Transgenic Plants

In order to see the effect of over-expression of PLC on the drought tolerance, both transgenics and control plants were subject to water deprivation. After 24 days of their growth under normal conditions, watering was stopped for next 24 days. Plants started drooping as the drought period progressed. After 24 days of drought, the plants severely withered on the pots but still some of the leaves looked green (FIG. 9). After 24 hours of 1 st 100 mL water application, one of the transgenics, recovered dramatically (FIG. 9). The other transgenic +ve for the insertion and rest of the plants including control did not recover the drought even after normal watering was resumed for several days (FIG. 9).

Sequence Listing Free Text

SEQ ID NO:1—Primer 1

SEQ ID NO:2—Primer 2

SEQ ID NO:3—PI-PLC DNA sequence (*B napus*)

SEQ ID NO:4 PI-PLC peptide sequence (*B napus*)

REFERENCES

Blatt Michael R. 2000. Cellular Signaling and Volume Control in Stomatal Movements in Plants. Annu. Rev. Cell Dev. Biol. 16:221-41.

Brearley C A and Hanke D E. 1996. Inositol phosphates in the duckweed *Spirodela polyrhiza* L. Biochem J. 314: 215-25.

Browse J and Xin Z. 2001. Temperature sensing and cold acclimation. Current opinion in plant biology 4:241-246.

Bunney T D, Watkins P A C, Beven A F, Shaw P J, Hernandez L E, Lomonossof G P, Shanks M, Peart J and Drobak B K. 2000. Association of Phosphatidylinositol 3-kinase with nuclear transcription sites in higher plants. The Plant cell. 12:1679-1688.

Kent D. Chapman. 1998. Phospholipase activity during plant growth and development and in response to environmental stress. Trends in Plant Science. Vol. 3. No. 11, 419-26.

Dewald D B, Torabinejad J, Jones C A, Shope J C, Cangelosi A R, Thompson J E, Prestwich G D and Hama H. 2001. Rapid accumulation of phosphatidylinositol 4,5-bisphosphate and inositol 1,4,5-trisphosphate correlates with calcium mobilization in salt-stressed *Arabidopsis*. Plant Physiology. 126:759-769.

Frank W, Munnik T, Kerkmann K, Salamini F and Bartels D. 2000. Water deficit triggers phospholipase D activity in the resurrection plant *Craterostigma plantagineum*. The Plant Cell. 12:111-123.

Franklin-Tong V E, Drobak B. K, Allan A C and Trewavas A J. 1996. Growth of pollen tubes of *Papaver rhoeas* is regulated by a slow moving calcium wave propagated by inositol 1,4,5-trisphosphate. Plant Cell 8:1305-1321.) Miege C and Marechal E. 1999. 1,2-sn-Diacylglycerol in plant cells: Product, substrate and regulator. Plant Physiology and Biochemistry. 37:795-808.

Hirayama T, Ohto C, Mizoguchi T, Shinozaki K. A gene encoding a phosphatidylinositol-specific phospholipase C is induced by dehydration and salt stress in *Arabidopsis thaliana*. Proc Natl Acad Sci U S A. 1995 Apr. 25; 92(9): 3903-7.

Hirayama T, Mitsukawa N, Shibata D and Shinozaki K. 1997. AtPLC2, a gene encoding phosphoinositide-specific phospholipase C, is constitutively expressed in vegetative and floral tissues in *Arabidopsis thaliana*. Plant Molecular Biology. 34:175-180.

Hong Z and Verma D P S. 1994. A phosphatidylinositol 3-kinase is induced during soybean nodule organogenesis and its associated with membrane proliferation. Proc. Natl. Acad. Sci. USA 91:9617-9621.

Kiegle E, Moore C A, Haseloff J, Tester M A and Knight M R. 2000. Cell-type-specific calcium response to drought, salt and cold in the *Arabidopsis* root. The Plant Journal. 23:267-278.

Kim D H, Eu Y-J, Yoo C M, Kim Y-W, Pih K T, Jin J B, Kim S J, Stenmark H and Hwang I. 2001. Trafficking of phosphatidylinositol 3-kinase from the trans-Golgi network to the lumen of the central vacuole in plant cells. The Plant Cell. 13:287-301.

Kopka J, Pical C, Gray J E and Muller-Roeber B. 1998. Molecular and enzymatic characterization of three phosphoinositide-specific phospholipase c isoforms from potato. Plant Physiology 116:239-250.

Kost B, Lemichez E, Spielhofer P, Hong Y, Tolias K, Carpenter C and Chua N-H. 1993. Rac homologues and compartmentalized phosphatidylinositol 4,5-bisphosphate act in a common pathway to regulate polar pollen tube growth. J. cell Biol. 145:317-330.

Loewus F A and Murthy P N. 2000. myo-inositol metabolism in plants. Plant Science 150:1-19; Nikawa J and Yamachita S. 1997. Phosphatidylinositol synthase from yeast. Biochimica et Biophysica Acta—Lipids and Lipid Metabolism. 1348:173-178.

Meijer H J, Berrie C P, Iurisci C, Divecha N, Musgrave A, Munnik T. 2001. Identification of a new polyphosphoinositide in plants, phosphatidylinositol 5-monophosphate (PtdIns5P), and its accumulation upon osmotic stress. Biochem J. 2001.60: 1-8

Miege C and Marechal E. 1999. 1,2-sn-Diaclyglycerol in plant cells: product, substrate and regulator. Plant Physiol. Biochem. 37: 795-808.

Mikami K, Katagiri T, Iuchi S, Yamaguchi-Shinozaki K, Shinozaki S. 1998. A gene encoding phosphatidylinositol-4-phosphate 5-kinase is induced by water stress and abscici acid in *Arabidopsis thaliana*. Plant J. 15: 563-568.

Moloney M M, Walker J M and Sharma K K. 1989. High efficiency transformation of *Brassica napus* using *Agrobacterium* vectors. Plant cell reports 8:238-242.

Morris D A. 1982. Hormonal regulation of sink invertase activity: Implications for the control of assimilate partitioning. In P F Waring, ed, Plant growth substances. Academic Press, London, pp 659-668

Morris D A, Arthur E D. 1984. An association between acid invertase activity and cell growth during leaf expansion in *Phaseolus vulgaris* L. J Expt Bot 35:1369-1379.

Munnik T, Irvine R F and Musgarve A. 1998. Phospholipid signalling in plants. Biochimica et Biophysica Ata. 1389. 222-272.

Munnik T, Meijer H J, Riet B t, Hrt H, Wolfganag F, Bartels D, and Musgrave A. 2000. Hyperosmotic stress stimulates phospholipase D activity and elevates the levels of phosphatidic acid and diacylglycerol pyrophosphate. The Plant Journal. 22:147-154.

Munnik T. 2001. Phosphatidic acid: an emerging plant lipid second messenger. Trends in plant science. 6:227-233.

Nanmori T, Taguchi W, Kinugasa M, Oji Y, Sahara S, Fukami Y and Kikkawa U. 1994. Purification and Characterization of protein kinase C from a higher plant, *Brassica campestris* L. Biochem Biophys Res Commun. 203:311-8

Ongusaha P P, Hughes P J, Davey J and Michell R H. 1998. Inositol hexakisphosphate in *Schizosaccharomyces pombe*: synthesis from Ins(1,4,5)P3 and osmotic regulation.
Biochem J. 335: 671-9.

Otterhag L, Sommarin M and Pical C. 2001. N-terminal EF-hand-like domain is required for phosphoinositide-specific phospholipase C activity in *Arabidopsis thaliana*, FEBS Letters. 497:165-170

Perera I Y, Heilmann I and Boss W. 1999. Transient and sustained increases in inositol 1,4,5-trisphosphate precede the differential growth response in gravistimulated maize pulvini. Proc. Natl. Acad. Sc. USA. 96:5838-5843.

Pical C, Westergen T, Dove S K, Larsson C, Sommarin M. 1999. Salinity and hyperosmotic stress induce rapid increases in phosphatidylinositol 4,5-bisphosphate, diacylglycerol pyrophosphate, and phosphatidylcholine in *Arabidopsis thaliana* cells. J Biol Chem. 274: 38232-40.

Plieth C, Hansen U-P, Knight H and Knight M R. 1999. Temperature sensing by plants: the primary characteristics of signal perception and calcium response. The Plant Journal. 18:491-497.

Raboy V, Gerbasi P F, Young K A, Stoneberg S D, Pickett S G, Bauman A T, Murthy P P, Sheridan W F and Ertl D S. 2000. Origin and seed phenotype of maize low phytic acid 1-1 and low phytic acid 2-1. Plant Physiol. 124: 355-68.

Rebecchi M L and Pentyala S N. 2000. Structure, Function and Control of Phosphoinositide-Specific Phospholipase C. Pyhiological Reviews. Vol. 80. 1291-1335

Roux M P, Kock J L and Nigam S. 1996. Phosphatidylinositol-3-kinse pathway is stimulated by fungal lipid containing cocoa butter equivalents (CBE) in Fmet-Leu-phe (FMLP)- and phorpbilester (PMA)-challenged human neutrophills. Adv Exp Med Biol. 416: 349-53.

Shank K J, Su P, Brglez I, Boss W F, Dewey R F and Boston R S. 200. Induction of lipid metabolic enzymes during the endoplasmic reticulum stress response in plants.
Plant Physiol. 126: 267-77.

Shi J, Gonzales R A and Bhattacharya M K. 1995 Characterization of a plasma membrane-associated phosphoinositide-specific phospholipase C from soybean. Plant Journal. 8:381-390.

Stephens I R and Irvine R F. 1990. Stepwise phosphorylation of myo-inositol leading to myo-inositol hexakisphosphate in *Dictyostelium*. Nature. 346: 580-3.

Stevenson J M, Perera I Y, Heilmann I, Persson S and Boss W. 2000. Inositol signaling and plant growth. Trends in Plant Science. 5:252-258.

Subramaniam R, Despres C and Brisson N. 1997. A functional homolog of mammalian protein kinase C participates in the elicitor-induced defense response in potato. Plant Cell. 9: 653-64.

Takahashi S, Katagiri T, Hirayama T, Yamaguchi-Shinozaki K and Shinozaki K. 2001. Hyperosmotic stress induces a rapid and transient increase in inositol 1,4,5-trisphosphate independent of abscisic acid in *arabidopsis* cell culture. Plant Cell Physiology. 42:214-222.

Walters P, Takegawa K, Emr S D, Chrispeels M J. 1994. AtVPS34, a phosphatidylinositol 3-kinase of *Arabidopsis thaliana*, is an essential protein with homology to a calcium-dependent lipid binding domain. Proc. Natl. Acad Sci. USA 91: 11398-11402.

Winicov I. 1998. New molecular approaches to improving salt tolerance in crop plants. Ann. Bot. 82:703-710

Xue H-W, Hosaka K, Plesch G and Muller-Roeber B. 2000. Cloning of *Arabidopsis thaliana* phosphatidylinositol synthase and functional expression in the yeast pis mutant. Plant Molecular Biology. 42:757-764).

York J D, Odom A R, Murphy R, Ives E B and Wente S R. 1999. A phospholipase C-dependent inositol polyphosphate kinase pathway required for efficient messenger RNA export. Science. 285: 96-100.

Yoshida K T, Wada T, Koyama H, Mizobuchi-Fukuoka R, Naito S. 1999. Temporal and spatial patterns of accumulation, of the transcript of Myo-inositol-1-phosphate synthase and phytin-containing particles during seed development in rice. Plant Physiol. 119: 65-72.

The invention claimed is:

1. A method of generating a transgenic plant having early maturation, increased growth rate, increased phytic acid content, increased heat tolerance, increased drought resistance and/or increased salt tolerance compared to an unmodified plant, the method comprising the steps of:
   (a) introducing into a plant cell a construct comprising, in addition to DNA sequences required for transformation and selection in plants, an expression construct including a DNA sequence encoding a Phosphoinositide-Specific Phospholipase C (PI-PLC) and obtained from a plant of genus *Brassica* operatively linked to a promoter for expressing said DNA sequence;
   (b) recovering a plant which contains the expression construct; and,
   (c) determining that the recovered plant has early maturation, increased growth rate, increased phytic acid content, increased heat tolerance, increased drought resistance and/or increased salt tolerance.

2. The method according to claim 1, wherein the expression construct further includes targeting means for targeting the activity of the PI-PLC expressed from the construct to guard cells of the plant.

3. The method according to claim 2, wherein the targeting means comprises an inducible, guard cell-specific promoter for specific expression of the DNA sequence within guard cells of the plant.

4. The method according to claim 2, wherein the targeting means comprises a signal sequence encoded by said expression construct comprising a series of amino acids covalently linked to said PI-PLC upon expression of said DNA sequence.

5. The method according to claim 1, wherein the DNA sequence encoding a Phosphoinositide-Specific Phospholipase C (PI-PLC) is obtained from a plant of species *Brassica napus*.

6. The method according to claim 1, wherein the promoter is selected from the group consisting of a constitutive promoter, an inducible promoter, a tissue specific promoter, a tissue-inspecific promoter, an organ specific promoter, and a cell-specific promoter.

7. The method according to claim 6, wherein the promoter is a constitutive.

8. The method according to claim 6, wherein the promoter expresses said DNA sequence encoding a Phosphoinositide-Specific Phospholipase C (PI-PLC) within guard cells of said transgenic plant.

9. The method according to claim 6, wherein the promoter is a guard-cell specific promoter derived from a plant of genus *Brassica*.

10. The method according to claim 1, wherein the DNA sequence encoding a Phosphoinositide-Specific Phospholipase C comprises SEQ ID NO: 3.

11. The method according to claim 2, wherein the DNA sequence encoding a Phosphoinositide-Specific Phospholipase C comprises SEQ ID NO: 3.

12. The method according to claim 3, wherein the DNA sequence encoding a Phosphoinositide-Specific Phospholipase C comprises SEQ ID NO: 3.

13. The method according to claim 7, wherein the DNA sequence encoding a Phosphoinositide-Specific Phospholipase C comprises SEQ ID NO: 3.

14. The method according to claim 8, wherein the DNA sequence encoding a Phosphoinositide-Specific Phospholipase C comprises SEQ ID NO: 3.

* * * * *